United States Patent
Ishida

[11] Patent Number: 5,879,369
[45] Date of Patent: Mar. 9, 1999

[54] CATHETER BALLOON AND BALLOON CATHETER

[75] Inventor: Toshinobu Ishida, Shizuoka-ken, Japan

[73] Assignee: Terumo Kabushiki Kaisha, Tokyo, Japan

[21] Appl. No.: 728,611

[22] Filed: Oct. 10, 1996

[30] Foreign Application Priority Data

Oct. 11, 1995 [JP] Japan .................................. 7-290377

[51] Int. Cl.$^6$ .................................................. A61M 25/10
[52] U.S. Cl. ............................ 606/194; 606/192; 604/96
[58] Field of Search ............................. 604/96; 606/194, 606/192

[56] References Cited

U.S. PATENT DOCUMENTS

| | | | |
|---|---|---|---|
| 5,270,086 | 12/1993 | Hamlin | 428/35.2 |
| 5,290,306 | 3/1994 | Trotta et al. | 604/96 X |
| 5,478,320 | 12/1995 | Trotta | 604/96 |
| 5,647,848 | 7/1997 | Jorgensen | 604/96 |

FOREIGN PATENT DOCUMENTS

| | | |
|---|---|---|
| 0 457 456 A1 | 11/1991 | European Pat. Off. . |
| 0 636 382 A1 | 2/1995 | European Pat. Off. . |
| 3-205064 | 9/1991 | Japan . |
| 4-144572 | 5/1992 | Japan . |
| 6-507101 | 8/1994 | Japan . |
| WO 92/19316 | 11/1992 | WIPO . |
| WO 95/09667 | 4/1995 | WIPO . |

*Primary Examiner*—Michael H. Thaler
*Attorney, Agent, or Firm*—Burns, Doane, Swecker & Mathis, LLP

[57] ABSTRACT

A catheter balloon having a base layer formed of a high-strength polymer and one or more covering layers formed over at least one surface of said base layer of the same flexible polymer or different flexible polymers having a elongation at break close to that of said high-strength polymer and being more flexible than said high-strength polymer, and has a wall thickness of 25 μm or thinner.

A balloon having a base layer formed of a high-strength polymer and one or more covering layers formed over at least one surface of said base layer of the same flexible polymer or different flexible polymers more flexible than said high-strength polymer, and has a wall thickness of 25 μm or thinner, said covering layer or covering layers together bearing 10% or more part of the bursting stress of the balloon.

A balloon catheter, especially blood vessel dilating catheter, equipped with any of the above balloons.

37 Claims, 5 Drawing Sheets

F I G. 9
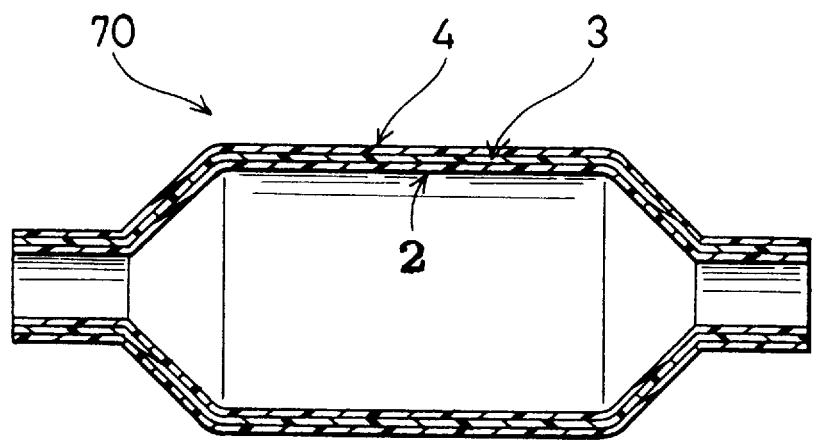

CATHETER BALLOON AND BALLOON CATHETER

BACKGROUND OF THE INVENTION

This invention relates to a catheter balloon and a balloon catheter using the same balloon, more specifically to a balloon for being attached to a catheter and used to dilate a stenosed part of a tubular organ such as a blood vessel and a balloon catheter using the same balloon, especially a blood vessel-dilating catheter.

In recent years, dilatation of a diseased part (stenosed or occluded part) in coronary artery by a catheter equipped with a balloon (blood vessel-dilating catheter) is more and more widely used as a method of treating cardiac infarction and angina pectoris.

A blood vessel-dilating catheter generally consists of a tubular catheter body, a dilating balloon attached to the distal end portion of the tubular catheter body, and a hub attached to the proximal end of the tubular catheter body.

For the material for the dilating balloon, polyolefin, polyethylene terephthalate (PET), polyamide, for example, are used.

Of polyolefin, low-density polyethylene (LPDE), high-density polyethylene (HDPE), straight-chain low-density polyethylene(LLDPE), and ethylene-vinyl acetate copolymer are used.

Although a balloon made of an olefin has a good flexibility and can be welded to the tubular catheter body, the resistance to internal pressure is comparatively small, and the change of diameter against a change of inflating pressure (compliance) is large.

A balloon made of PET generally has a high strength, and hence a high resistance to internal pressure and a small compliance. However, the balloon is stiffs, and the tracking capability (capability of a balloon to advance along flexures in a tubular organ) is low. If the wall of the balloon is made thin so as to increase the tracking capability, the resistance to internal pressure becomes low, and the balloon becomes pinhole prone.

A balloon made of a nylon or a polyamide has intermediate properties between the properties of a balloon made of a polyolefin and those of a balloon made of PET. If the wall of this balloon is made thin, the balloon becomes pinhole prone. If the wall of this balloon is made thick, on the other hand, the tracking capability becomes inadequate.

To solve these problems with conventional catheter balloons, especially a catheter balloon made of PET, a multilayer balloon made of PET as the base layer and polyethylene or other plastic for an additional layer is disclosed in Patent Application Lay-open Gazette No. 1991-205064 and Patent Application Publication Gazette No. 1994-507101. These balloons were proposed in order to improve the weldability of a balloon made of PET to a tubular catheter body or to increase the resistance to pinholes. To increase the flexibility and the strength of the balloon simultaneously is not intended.

In the balloons disclosed in the above gazettes, the PET layer must be thick to obtain a balloon with a high strength (resistance to internal pressure), the balloon becomes stiff and the tracking capability of the balloon decreases If the PET layer is made thin to obtain a flexible balloon, the strength of the balloon decreases and the balloon becomes pinhole prone.

The object of this invention is to provide a new improved balloon which has an adequate strength (resistance to internal pressure) and is flexible enough to give a satisfactory tracking capability.

SUMMARY OF INVENTION

The above problems with conventional catheter balloons are solved by the following catheter balloons of this invention.

The first catheter balloon of this invention comprising a cylindrical portion and attaching portions for a catheter, said catheter balloon having a base layer formed of a high-strength polymer and one or more covering layers formed over at least one surface of said base layer of the same flexible polymer or different flexible polymers having a elongation at break close to that of said high-strength polymer and being more flexible than said high-strength polymer, and said cylindrical portion having a wall thickness of 25 $\mu$m or thinner.

The second catheter balloon of this invention comprising a cylindrical portion and attaching portions for a catheter, said catheter balloon having a base layer formed of a high-strength polymer and one or more covering layers formed over at least one surface of said base layer of the same flexible polymer or different flexible polymers more flexible than said high-strength polymer, and said covering layer or covering layers together bearing 10% or more part of the bursting stress of the balloon, and said cylindrical portion having a wall thickness of 25 $\mu$m or thinner.

The third catheter balloon comprising a cylindrical portion and attaching portions for a catheter, said catheter balloon having a base layer formed of a high-strength polymer, a first covering layer formed over the outside surface of said base layer of an flexible polymer having a elongation at break close to that of the high-strength polymer and being more flexible than the high-strength polymer, and a second covering layer formed over the outside surface of said first covering layer of another flexible polymer more flexible than said flexible polymer for said first covering layer.

The first balloon catheter comprises of a tubular catheter body and a balloon attached to a distal end portion of said tubular catheter body, and said balloon comprising a cylindrical portion and attaching portions for a catheter, said catheter balloon having a base layer formed of a high-strength polymer and one or more covering layers formed over at least one surface of said base layer of the same flexible polymer or different flexible polymers having a elongation at break close to that of said high-strength polymer and being more flexible than said high-strength polymer, and said cylindrical portion having a wall thickness of 25 $\mu$m or thinner. The second balloon catheter comprises of a tubular catheter body and a balloon attached to a distal end portion of said tubular catheter body, and said balloon comprising a cylindrical portion and attaching portions for a catheter, said catheter balloon having a base layer formed of a high-strength polymer and one or more covering layers formed over at least one surface of said base layer of the same flexible polymer or different flexible polymers more flexible than said high-strength polymer, and said covering layer or covering layers together bearing 10% or more part of the bursting stress of the balloon, and said cylindrical portion having a wall thickness of 25 $\mu$m or thinner.

The third balloon catheter comprises of a tubular catheter body and a balloon attached to a distal end portion of said tubular catheter body, and said balloon comprising a cylindrical portion and attaching portions for a catheter, said catheter balloon having a base layer formed of a high-strength polymer, a first covering layer formed over the outside surface of said base layer of an flexible polymer having a elongation at break close to that of the high-strength polymer and being more flexible than the high-strength polymer, and a second covering layer formed over the outside surface of said first covering layer of another flexible polymer more flexible than said flexible polymer for said first covering layer.

BRIEF DESCRIPTION OF THE DRAWINGS

FIG. 9 is another embodiment of the catheter balloon of this invention.

DETAILED DESCRIPTION OF THE PREFERRED EMBODIMENTS

The catheter balloon and the balloon catheter of this invention are described below in detail using the embodiments shown in the attached Figures.

Figure 1:
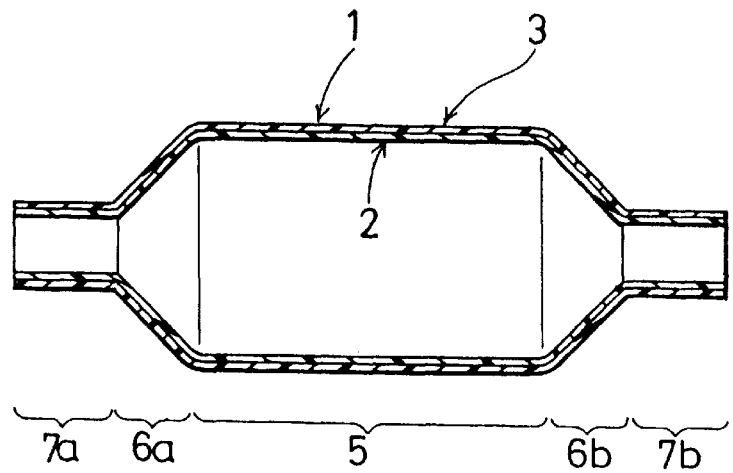
FIG. 1 is a sectional view of an embodiment of the catheter balloon of this invention.

FIG. 1 shows an embodiment of the catheter balloon of this invention.

The catheter balloon 1 of this embodiment comprises a cylindrical portion 5 and attaching portions for a catheter 7a and 7b. The catheter balloon 1 has a base layer 2 made of a high-strength polymer and a covering layer 3 formed over at least one surface of the base layer 2 of a flexible polymer having a elongation at break (in other words, elongation after fracture, percentage elongation after fracture or percentage elongation at break) close to that of the high-strength polymer and being more flexible than the high-strength polymer. The cylindrical portion 5 has a wall thickness of 25 μm or thinner.

The balloon 1 may be a multilayer balloon which consists of a base layer 2 made of a high-strength polymer and a covering layer 3 formed over at least one surface of the base layer 2 of a polymer more flexible than the high-strength polymer, and has a wall thickness of 25 μm or thinner, the covering layer bearing 10% or greater part of the bursting stress of the balloon.

The balloon 1 is capable of being folded, and is folded around the circumferential surface of the tubular catheter body when it is not inflated.

The balloon 1 has a cylindrical portion 5, tapered portions 6a and 6b extending from the front and rear ends of the cylindrical portion 5, respectively, and attaching portions for a catheter 7a and 7b extending from the thin end of the tapered portions 6a and 6b.

The cylindrical portion 5 is a portion for dilating a stenosed part of a tubular organ such as a blood vessel, ureter, and bile duct, and has a largest, substantially uniform diameter throughout its length. The cylindrical portion 5 is not necessarily a circular cylinder, but may be a prism.

The tapered portions 6a and 6b extend from each end of the cylindrical portion 5 and become gradually smaller in diameter.

The attaching portions 7a and 7b are small-diameter portions for attaching the balloon 1 to the tubular catheter body. They extend from the thin end of the tapered portions 6a and 6b, respectively, and have a substantially uniform interior diameter.

The shapes of the front and rear tapered portions 6a and 6b and those of the front and rear attaching portions 7a and 7b may be different.

The overall length of the balloon 1 is within the range of 5.0 to 120.0 mm, preferably 15.0 to 100.0 min. The cylindrical portion 5 of the balloon 1 is within the range of 1.0 to 35.0 mm, preferably 1.5 to 30.0 mm in exterior diameter and within the range of 3.0 to 80.0 mm, preferably 10.0 to 75.0 mm in length. The wall thickness of the balloon 1, at least the cylindrical portion 5, is 25 μm or thinner. By making the wall of the balloon thus thin, the flexibility and hence the tracking capability of the balloon is greatly increased. The wall thickness within the range of 10 to 20 μm is especially preferable.

The wall thickness of the attaching portions 7a and 7b may be the same as that of the cylindrical portion 5, or may be thicker than that of the cylindrical portion 5, even thicker than 25 μm, to make the attaching process of the balloon to a tubular catheter body easier and to increase the strength of attachment.

The wall thickness of the tapered portions 6a and 6b may be the same as that of the cylindrical portion 5b, or may be thinner than that of the cylindrical portion 5 to make folding of the balloon easier. Since it is the distal-side tapered portion 6a that is important to smooth insertion of the catheter into a tubular organ, the wall thickness of the distal-side tapered portion 6a or part of it may be made thinner. When making the wall thickness of the tapered portions 6a and 6b thinner than that of the cylindrical portion 5, the wall thickness of the tapered portions 6a and 6b are preferably thinner by 1 to 5 μm than that of the cylindrical portion 5.

The balloon 1 is preferably biaxially stretched. Biaxial stretch means stretching the balloon 1 in the direction of the longitudinal axis and in the direction perpendicular to the longitudinal axis. By this biaxial stretch, the balloon 1 becomes stronger, and hence can be made thinner. Further, the tapered portions 6a and 6b are preferably stretched once more to make the wall thickness thinner by stretching once more.

The balloon 1 has a multilayer structure which consists of a base layer 2 made of a high-strength polymer and a covering layer 3 formed over at least one surface of the base layer 2 of a flexible polymer more flexible than the high-strength polymer. In the embodiment shown in FIG. 1, the inner layer is the base layer, and the outer layer is the covering layer.

The base layer 2 is formed of a high-strength polymer or the high-strength polymer for the base layer, stretchable plastics are preferable. For example, polyethylene terephthalate (PET), polyester obtained by replacing the principal acid component or principal glycol component of polyethylene terephthalate (polyethylene terephthalate copolymer), a mixture of the preceding polymers, polyamide (12-nylon, 11-nylon, and MXD 6-nylon), and polyarylenesulfide such as PPS (polyphenylenesulfide) can be used.

For the acid component to replace the principal acid component of polyethylene terephthalate with, isophthalic acid, orthophthalic acid, naphthalenedicarboxylic acid, paraphenylenedicarboxylic acid, cyclohexanedicarboxylic acid, succinic acid, glutaric acid, adipic acid, suberic acid, azelaic acid, sebacic acid, dodecanedione acid, trimellitic acid, pyromellitic acid, sulfoisophthalic acid, and their salt, for example, can be used.

For the glycol component to replace the principal glycol component of polyethylene terephthalate with, propylene glycol, butanediol, pentanediol, hexanediol, neopentyl glycol, diethylene glycol, triethylene glycol, polyethylene glycol, polytetramethylene glycol, cyclohexanedimethanol, ethylene oxide-added bisphenol A, trimethylolpropane, and pentaerythritol, for example, can be used.

The polymer for the covering layer 3 is preferably a flexible polymer of the same group as the high--strength polymer used for the base layer 2, and more preferably thermoplastic and stretchable. By using a polymer of the same group, the weldability or adherence of the covering layer 3 to the base layer 2 increases. A flexible polymer with a weldability or adherence increased by modification may also be used. Further, a polymer not of the same group as the high-strength polymer may be used if it has a good weldability or adherence to the base layer 2. A bonding layer may be formed on the base layer 2 or the covering layer 3, and in this case the polymer for the covering layer 3 must not be a polymer of the same group as that for the base layer.

For the flexible polymer (high-molecular elastomer) for forming the covering layer, polyester elastomer (polyester elastomer which has an aromatic polyester as the hard segment and an aliphatic polyether as the soft segment or polyester elastomer which has an aromatic polyester as the hard segment and an aliphatic polyester as the soft segment, for example), and polyamide elastomer (polyamide elastomer which has a polyamide (12-nylon, for example) as the hard segment and a plasticizer, polyether, or polyester as the soft segment, for example) can be used.

That the elongation at break of the base layer 2 is close to that of the covering layer 3 means that separation of the two layers hardly occur. In other words, the elongation it break of the base layer 2 is close to that of the covering layer 3 means that a elongation of the base layer is close to a elongation of the covering layer until the balloon has burst.

To make the elongation at break of the base layer 12 and that of the covering layer 3 close to each other, the materials for the base layer 2 and the covering layer 3 must be suitably selected. The elongation at break is a property which can be used for the selection of the material. It is desirable that the ratio of the elongation at break of the high-strength polymer to that of the flexible polymer is preferably within the range of about 1:0.7 to 1:1.3. That is, it the difference of elongation at break between both polymers is 30% or smaller, their elongation at breaks are adequately close to each other. More preferably the difference of elongation at break is 20% or smaller.

The percentage elongation at break of the flexible polymer is preferably within the range of 300 to 700% (ASTM D638). If the elongation at break is within this range, the flexible polymer has an adequate flexibility A more preferable range of the percentage elongation at break of the flexible polymer is 350 to 600% (ASTM D638).

The percentage elongation at break of the high-strength polymer is preferably within the range of 300 to 700% (ASTM D638), more preferably 400 to 600% (ASTM D638).

Another property related to the elongation at break is the tensile fracturing strength. The ratio of the tensile fracturing strength of the high-strength polymer to that of the flexible polymer is preferably within the range of about 1:0.7 to 1:1.3. That is, the difference of tensile fracturing strength between both polymers is preferably 30% or smaller.

The tensile fracturing strength of the flexible polymer is preferably within the range of 300 to 400 kg/cm$^2$ (ASTM D638). If the elongation at break is within this range, the flexible polymer has an adequate strength.

The flexural elasticity of the flexible polymer is preferably within the range of 1,000 to 15,000 kg/cm$^2$ (ASTM D790). If the flexural elasticity is within this range, the flexible polymer has an adequate flexibility. A more preferable range of the flexural elasticity of the flexible polymer is 2,000 to 13,000 kg/cm$^2$ (ASTM D790).

Preferable combinations of the plastics for the base layer and the covering layer are polyethylene terephthalate for the base layer and polyester elastomer for the covering layer, or a polyamide for the base layer and a polyamide elastomer for the covering layer.

The wall thickness of the base layer is preferably within the range of 3 to 15 $\mu$m, especially 4 to 12 $\mu$m. The wall thickness of the covering layer is preferably within the range of 1 to 15 $\mu$m, especially 2 to 12 $\mu$m.

The ratio of the wall thickness of the base layer to that of the covering layer is preferably within the range of 1:0.3 to 1:2, especially 1:0.5 to 1:1.5. The wall thicknesses of these layers are determined, taking the plastics used into consideration, so that the covering layer bears 10%, preferably 20%, and more preferably 30% or more part of the bursting stress of the balloon.

That the covering layer bears 10% or more part of the bursting stress means that when the bursting strength of a balloon having the base layer and covering layer is X kg/cm$^2$ and the bursting strength of a balloon having the base layer only is Y kg/cm$^2$, Y/X is equal to or smaller than 0.9.

The balloon 1 is preferably biaxially stretched. It is especially preferable that both the base layer and the covering layer are biaxially stretched.

Figure 2:
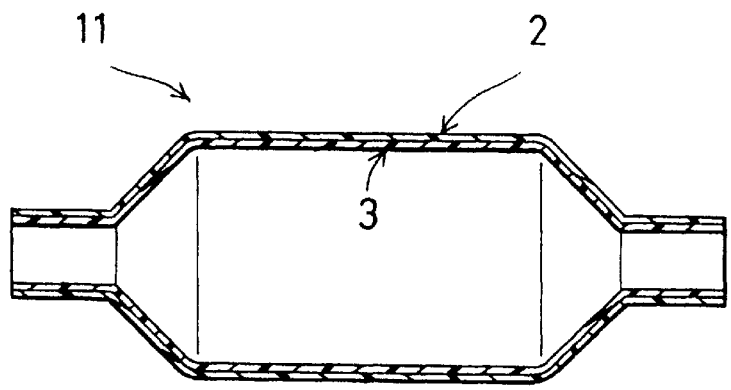
FIG. 2 is a sectional view of another embodiment of the catheter balloon of this invention.

FIG. 2 shows another embodiment of the balloon of this invention. In the balloon of this embodiment 11, the outer layer is the base layer 2, and the inner layer is the covering layer 3.

Figure 3:
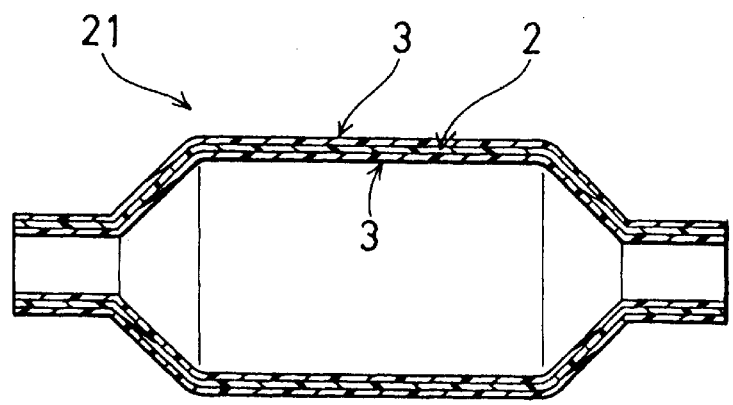
FIG. 3 is a sectional view of another embodiment of the catheter balloon of this invention.

FIG. 3 shows another embodiment of the balloon of this invention. The balloon 21 of this embodiment has a middle layer which is the base layer 2, and an outer layer and an inner layer which are the cover layer 3. In this embodiment, the outer layer and inner layer together bear 10% or more part of the bursting stress of the balloon.

FIG. 9 shows another embodiment of the balloon of this invention. The balloon 70 of this embodiment has a base layer 2 formed of a high-strength polymer, a first covering layer 3 formed over the outside surface of the base layer 2 of a flexible polymer which has a elongation at break close to that of the high-strength polymer and is more flexible than the high-strength polymer, and a second covering layer 4 formed over the outside surface of the first covering layer 3 of a high-flexibility polymer more flexible than the flexible polymer for the first covering layer 3. The wall thickness of the balloon is preferably 25 $\mu$m or less.

By thus forming the second covering layer more flexible than the first covering layer over the outside surface of the fist covering layer, the flexibility and hence the tracking capability of the balloon further increase.

Polymers suited to the high-strength polymer and the flexible polymer are the same as those described above. The size and wall thickness of the balloon of this embodiment are also the same as those of the balloon described above.

For the high-flexibility polymer for the second covering layer 4, polymers more flexible than those for the flexible polymer are used.

For example, polyester elastomer (polyester elastomer which has an aromatic polyester as the hard segment and an aliphatic polyether as the soft segment or polyester elastomer which has an aromatic polyester as the hard segment and an aliphatic polyester as the soft segment, for example), or polyamide elastomer (polyamide elastomer which has a polyamide (12-nylon, for example) as the hard segment and a plasticizer, polyether, or polyester as the soft segment, for example) can be used.

The ratio of the tensile fracturing strength of the flexible polymer to that of the high-flexibility polymer is preferably within the range of about 1:0.7 to 1:1.3, preferably 1:0.8 to 1:1.2.

Further, the flexural elasticity of the high-flexibility polymer is preferably within the range of 800 to 4,000 kg/cm$^2$ (ASTM D790). If the flexural elasticity is within this range, the high-flexibility polymer has an adequate flexibility. The flexural elasticity of the high-flexibility polymer is more preferably within the range of 1,000 to 2,000 kg/cm$^2$ (ASTM D790).

The tensile fracturing strength of the high-flexibility polymer is preferably within the range of 200 to 400 kg/cm$^2$ (ASTM D638).

The ratio of the elongation at break of the flexible polymer to that of the high-flexibility polymer is preferably within the range of about 1:0.7 to 1:1.3, preferably 1:0.8 to 1:1.2.

The elongation at break of the high-flexibility polymer is preferably within the range of 300 to 700 kg/cm$^2$ (ASTM D638). If the elongation at break is within this range, the high-flexibility polymer has an adequate flexibility. A more preferable range of the elongation at break of the high-flexibility polymer is 350 to 600% (ASTM D638).

It is also desirable for the balloon of this embodiment that the first covering layer hears 10%, preferably 20% or more part of the bursting stress of the balloon. The same part of the stress may be born by the first and second covering layers together.

The outside surface of the balloon 1 may be coated with a biocompatible plastic, especially an anti-thrombogenic property. For example, polyhydroxyethylmethacrylate or hydroxyethylmethacrylate-styrene copolymer (HEMA-St-HEMA block copolymer, for example) is suited to this purpose.

Further, to make insertion into a guide catheter and a blood vessel easier, the outside surface of the balloon is preferably treated so as to become slippery when it gets in touch with blood or other body fluid.

This treatment is performed by coating or fixing a hydrophilic plastic, such as poly(2-hydroxyethylmethacrylate), polyhydroxyethylacrylate, hydroxypropylcellulose, copolymer of methylvinylether and maleic anhydride, polyethyleneglycol, polyacrylamide, polyvinylpiroridon or dimethylacrylamide-glycidylmethacrylate copolymer (for example, dimethylacrylamide-glycidylmethacrylate random copolymer).

Next, the manufacturing process of the catheter balloon of this invention is described below.

First, a two-layer high-polymer tube (parison) is made of a stretchable high-strength polymer and a stretchable flexible polymer.

Next, the parison is heated at a temperature within the range from the second-order transition temperature to the first-order transition temperature of both polymers. The heated parison is stretched in the direction of its axis and then inflated radially to biaxially stretch. The stretched and inflated parison is cooled below the second-order transition temperatures of both polymers and then deflated. Thus a biaxially-stretched balloon which has a cylindrical portion of a substantially uniform exterior diameter, tapered portions extending from each end of the cylindrical portion, and attaching portions extending from the thin end of each tapered portion is formed. The tapered portions of the balloon may be stretched again to make their wall thickness thinner as necessary. After the tapered portions are stretched, the balloon is inflated and heated above the second order transition temperatures of the polymers while being inflated, and then cooled below the second order transition temperatures.

Hereinafter, each step of the above process is described in detail.

In the first step, a tubular parison 17 is made of the two stretchable polymers for the base layer and the covering layer of the balloon 1 The tubular parison 17 is preferably made by two-color extrusion. The parison may also be made by forming a tube of the polymer for the inner layer (base layer or covering layer) and then forming a layer over the outside surface of the tube of the polymer for the outside layer (covering layer or base layer).

Figure 4:
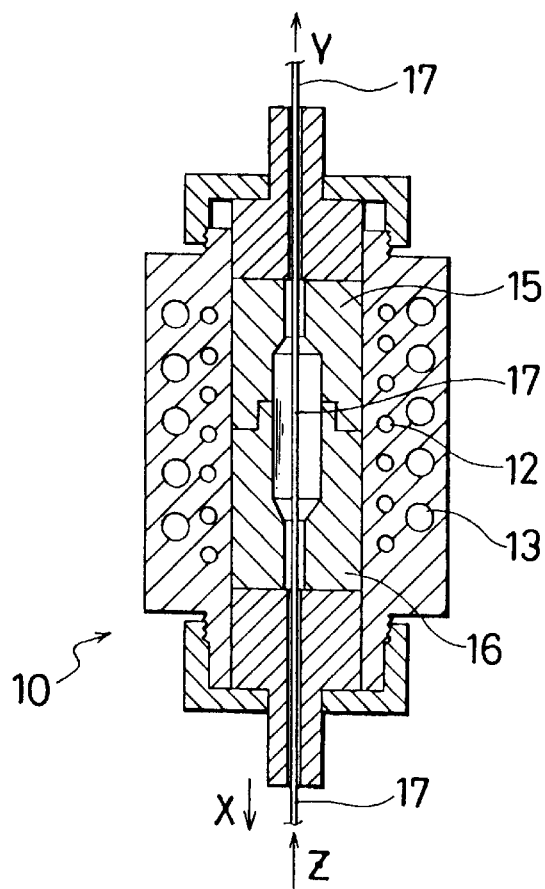
FIG. 4 is a diagrammatic drawing of the balloon-forming metal mold.

In the next step, the tube 17 is put in a balloon-forming metal mold 10 shown in FIG. 4, and one end of the tube 17 is closed in an air-tight fashion, for example, by heating, high-frequency waves, or forceps. The metal mold 10 is provided with a heater 12 for heating and a cooling conduit 13 for cooling.

The metal mold 10 consists of divided metal molds 15 and 16, the inside surfaces of which form the external shape of the balloon when they are fit together.

As shown in FIG. 4, the part of the tube 17 to be formed into the balloon is heated to a temperature within the range from the second-order transition temperature to the first-order transition temperature of the polymers, specifically a temperature a little higher than the second-order transition temperatures of both polymers by using the heater 12. While heated, the tube 17 is stretched in its axial direction by pulling it in the directions indicated by arrows X and Y. The tube is then inflated by introducing pressurized air from one end indicated by Z so that the heated part of the tube 17 is tightly pressed against the inside surface of the metal mold. While inflated, the tube 17 is cooled below the second-order transition temperatures by flowing a cooling liquid in the cooling conduit 13 The tube 17 may also be cooled by free cooling. The air in the tube 17 is then released, and the tube 17 is taken out from the metal mold 10. Both end portions of the tube 17 not making up the balloon are cut off. Thus the basic shape of the balloon of this invention as shown in FIG. 4 is formed. This stretching process may be repeated two or more times to form the balloon of a desired wall thickness.

Figure 5:
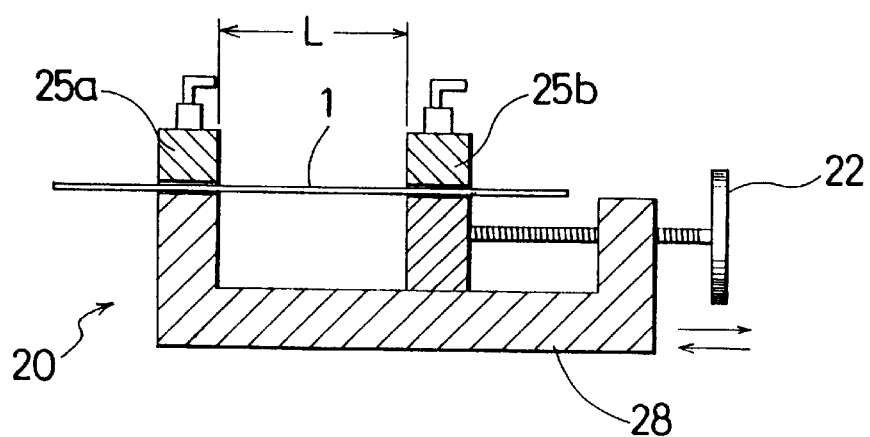
FIG. 5 is a diagrammatic drawing of the balloon-stretching jig.

The tapered portions 6a and 6b of the biaxially-stretched balloon may be stretched again to make the wall thicknesses thinner. FIG. 5 is a sectional view of a jig for stretching the tapered portions 6a and 6b, or both the tapered portions 6a and 6b and the attaching portions 7a and 7b. The jig 20 has two clamps 25a and 25b for firmly holding the balloon. One clamp 25b is movably supported on a base 28 and can be moved toward and away from the other clamp 25a by turning a crank 22 on the end of a threaded bar.

Next, the balloon catheter of this invention is described below using the embodiment shown in FIGS. 6 to 8. The balloon catheter is a blood-vessel dilating catheter.

Figure 6:
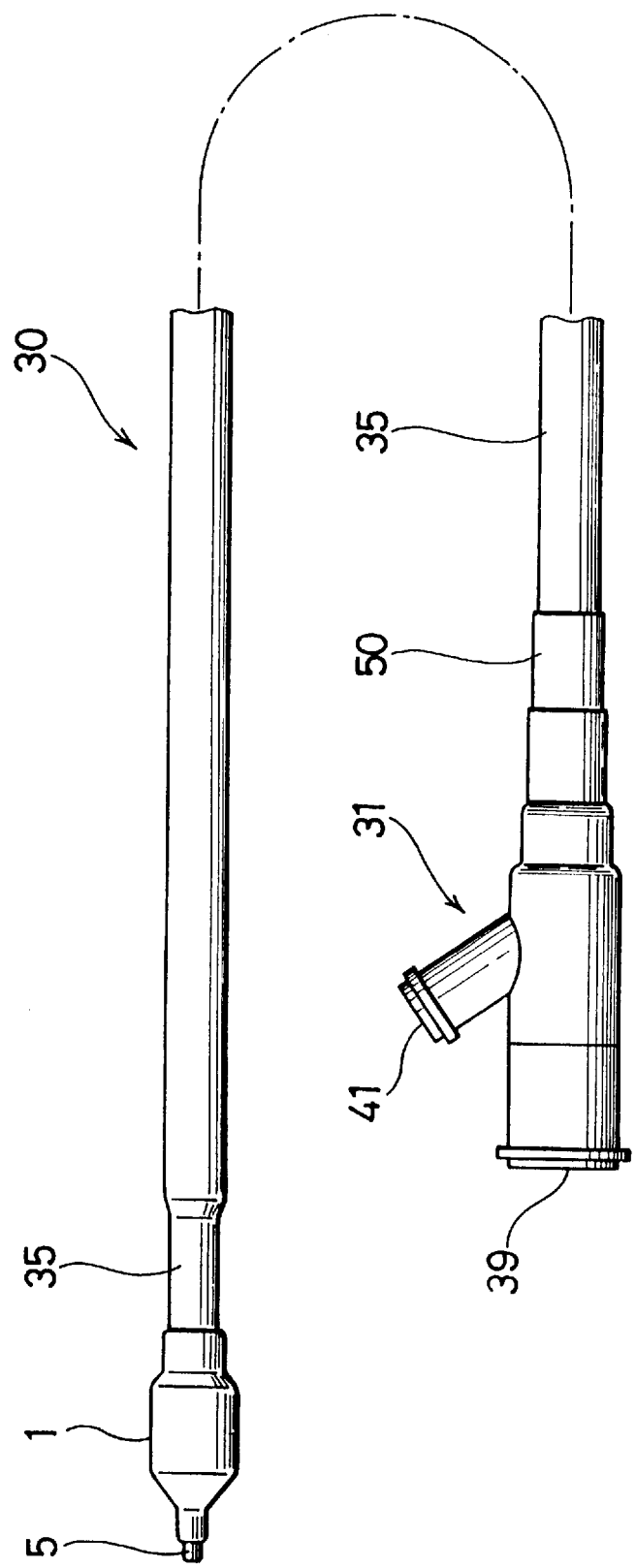
FIG. 6 is a perspective view of the blood-vessel dilating catheter.

FIG. 6 is a perspective view of an embodiment of the balloon catheter of this invention which is a blood vessel-dilating catheter. FIG. 7 is a sectional view of the distal end portion of the balloon catheter, and FIG. 8 is a sectional view of the proximal end portion of the balloon catheter.

The balloon catheter 30 of this invention comprises of a tubular catheter body, a balloon 1 attached to the distal end portion of the tubular catheter body, and a hub 31 attached to the proximal end of the tubular catheter body as shown in FIG. 6.

Specifically, the tubular catheter body comprises an inner tube 24 and an outer tube 35. The inner tube 24 has a first lumen 34 with the distal end open, and is held inside the outer tube 35 to form a second lumen 36 between it and the outer tube 35. The distal end portion of the inner tube 24 protrudes from the distal end of the outer tube 35.

The front attaching portion 7a of the balloon 1 is attached to the distal end portion of the inner tube 24, and the rear attaching portion 7b is attached to the distal end portion of the outer tube 35. The inside of the balloon connects with the second lumen 36 near the rear end of the inflating portion of the balloon 1.

The first lumen 34 of the inner tube 24 is used for passing a guide wire through, and connects with a first bore 39 in the branched hub 31 (described later) which serves for a guide wire port.

The inner tube 24 has an outside diameter within the range of 0.30 to 2.50 mm, preferably 0.40 to 2.00 mm and an inside diameter within the range of 0.20 to 2.35 mm, preferably 0.25 to 1.70 mm.

For the material for the inner tube 24, plastics with a certain amount of flexibility are preferable. For example, thermoplastic resins such as polyolefin (polyethylene, polypropylene, ethylene-propylene copolymer, ethylene-vinyl acetate copolymer, etc.), polyvinyl chloride, polyurethane, polyamide, polyamide elastomer, and polyester elastomer can be used.

The outer tube 35 encases the inner tube 24. The distal end of the outer tube 35 is retreated from the distal end of the inner tube by a predetermined distance so as to allow the distal end portion of the inner tube 24 to protrude from the distal end of the outer tube. A second lumen 36 is formed between the inside surface of the outer tube 35 and the outside surface of the inner tube 24. The distal end of the second lumen 36 connects with the rear end of the inside of the balloon 1, and the proximal end connects with a second bore 41 in the branched hub 31 which serves for an injection port of a liquid (contrast medium, for example) for inflating the balloon.

The outer tube 35 has an outside diameter within the range of 0.50 to 4.30 mm, preferably 0.60 to 4.00 mm and an internal diameter of 0.40 to 3.80 mm, preferably 0.50 to 3.00 mm.

For the material for forming the outer tube 35, materials with a certain amount of flexibility are preferable. For example, thermoplastic resins such as polyolefin polyethylene, polypropylene, ethylene-propylene copolymer, ethylene-vinyl acetate copolymer, etc.), polyvinyl chloride, polyurethane, polyamide, polyamide elastomer, and polyester elastomer can be used.

For the balloon 1, the catheter balloon of this invention is used.

The front attaching portion 7a of the balloon 1 is attached to the distal end portion of the inner tube 24, and the rear attaching portion 7b to the distal end portion of the outer tube 35, in a liquid-tight fashion by means of an adhesive or welding.

Figure 7:
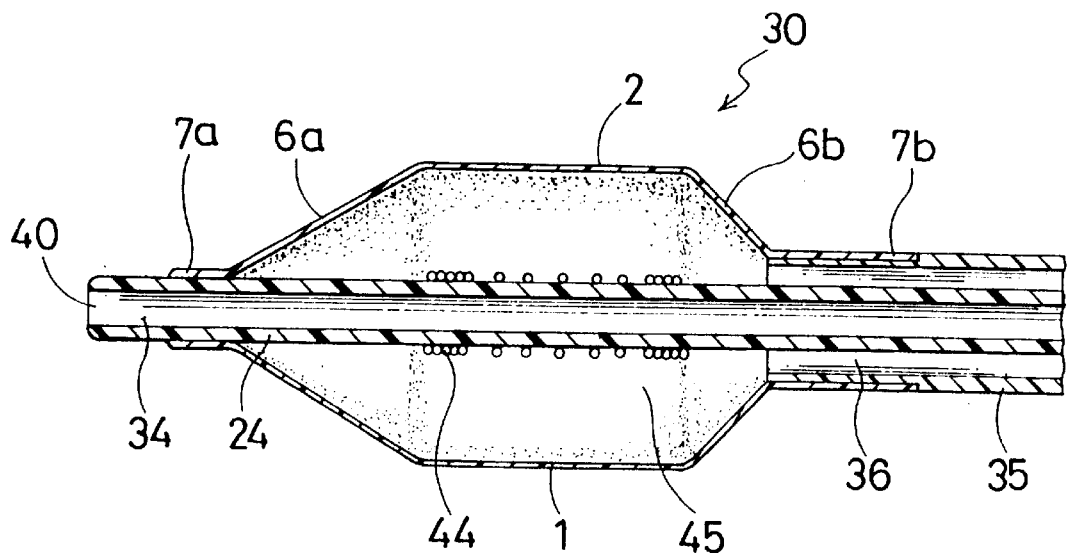
FIG. 7 is a sectional view of the distal end portion of the catheter of FIG. 6.

The balloon 1 forms a hollow space 45 between its inside surface and the outside surface of the inner tube 24 as shown in FIG. 7. This hollow space 45 connects with the second lumen 36 at its rear end all around the inner tube.

It is preferable that a marker 44 is attached on the outside surface of the inner tube 24 in order to make the position of the cylindrical portion 5 of the balloon 1 visible by means of X rays. The maker 44 preferably indicates the length and ends of the cylindrical portion 5 of the balloon 1. For the material of the marker 44, materials comparatively opaque to X rays such as gold, platinum, tungsten, stainless-steal, and their alloy and silver-palladium alloy are preferable. A preferable configuration of the marker 44 is a coil spring, especially a coil spring which has closely wound portions of a length of 1 to 4 mm, preferably 2 to 3 mm at both ends as shown in FIG. 7. This closely wound portions at the ends of a spring coil increases the visibility of the position of the cylindrical portion 5 of the balloon 1 by means of X rays. The coil-spring configuration allows the marker to serve as a reinforcement and prevents collapsing of the inner tube 24 at bends in a tubular organ. Instead of a single coil spring, the maker 44 may consist of two or more marking pieces.

When a single closely-wound coil spring is fit on the outside surface of the inner tube 24, the capability of this portion of bending without collapsing is considerably increased.

The cross section of the wire material for the coil spring may be circular, rectangular, elliptic, or any other shapes.

The branched hub 31 consists of an inner-tube hub 52 and an outer-tube hub 53.

The inner-tube hub 52 is attached to the proximal end of the inner tube 24 and has a first bore 39 which connects with the first lumen 34 and serves for a guide wire port.

The outer-tube hub 53 is attached to the proximal end of the outer tube 35 and has a second bore 41 which connects with the second lumen 36 and serves for a injection port.

The inner-tube hub 52 and outer-tube hub 53 are joined together.

Figure 8:
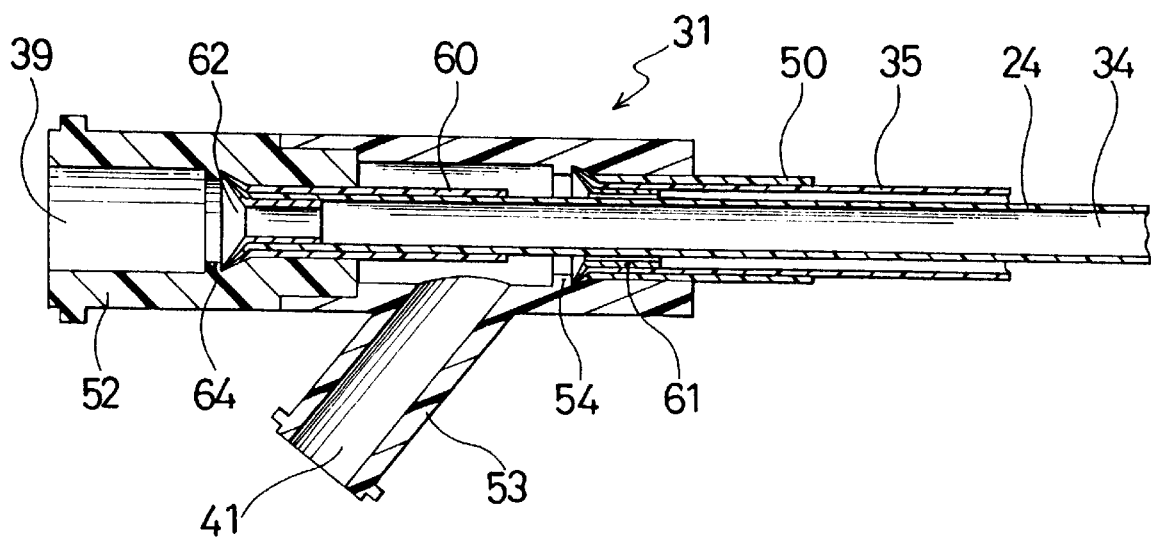
FIG. 8 is a sectional view of the proximal end portion of the catheter of FIG. 6.

In the embodiment shown in FIG. 8, a reinforcing tube 50 for preventing bending is fitted on the proximal end portion of the outer tube 35. The reinforcing tube 50 is made of a heat-shrinkable material and fitted on the outer tube 35 by forming it a little greater in interior diameter than the exterior diameter of the outer tube 35, putting it on the outer tube, and heating it (by blowing hot air, for example) The proximal end of the outer tube 35 is secured to the outer-tube hub 53 by means of a clamping member 61. The clamping member 61 has a portion of about the same exterior diameter as the interior diameter of the outer tube 53 and inserted in the outer tube, and a rear end portion of a diameter greater than the outside diameter of the reinforcing tube 50. The clamping member 61 is inserted into the proximal end of the outer tube 35, and the outer tube 35 is then inserted into the outer-tube hub 53 with the distal end leading and passed through it until the larger-diameter rear end portion of the clamping member 61 clears a circular projection 54 in the inside surface of the outer-tube hub 53. An adhesive may be applied between the inside surface of the outer-tube hub 53 and the outside surface of the reinforcing tube 50.

For the material for the outer-tube hub 53, thermoplastic resins such as polycarbonate, polyamide, polysulfone, polyacrylate and methacrylate-butylene-styrene copolymer are preferable.

A reinforcing tube 60 is fitted on the proximal end portion of the inner tube 24. The reinforcing tube 60 is made of a heat-shrinkable material and fitted on the inner tube 24 by forming it a little greater in interior diameter than the exterior diameter of the inner tube 24, putting it on the inner tube, and heating it (by blowing hot air, for example). The proximal end of the inner tube 24 is secured to the inner-tube hub 52 by means of a clamping member 62. The clamping member 62 has a portion of about the same exterior diameter as the interior diameter of the inner tube 24 and inserted in the inner tube and a rear end portion of a diameter greater than the outside diameter of the reinforcing tube 60. The clamping member 62 is inserted into the proximal end of the inner tube 24, and the inner outer tube 24 is then inserted into the inner-tube hub 52 with the distal end leading and passed through it until the larger-diameter rear end portion of the clamping member 62 clears a circular projection 64 in the inside surface of the inner-tube hub 52. An adhesive may be applied between the inside surface of the inner-tube hub 52 and the outside surface of the reinforcing tube 60.

For the material for the inner-tube hub 52, thermoplastic resins such as polycarbonate, polyamide, polysulfone, polyacrylate and methacrylate-butylene-styrene-copolymer are preferable.

The inner-tube hub 52 and the outer-tube hub 53 are connected together by fitting the front end portion of the inner-tube hub 52 in the rear end portion of the outer-tube hub 53 as shown in FIG. 8. An adhesive may be applied between the connecting portions.

Instead of connecting such a branched hub, tubular port members with a bore in their rear end may be connected to the inner and outer tubes in a liquid-tight fashion.

Next, examples of the balloon of this invention are described below.

EXAMPLE 1

A high-molecular polyethylene terephthalate (PET) with a specific viscosity of about 1.1[JAPAN UNIPET Co., Ltd., Product Name: UNIPET RT580CA, Tensile fracturing strength: 600 kg/cm$^2$ (ASTM D638), Flexural elasticity: 24,000 kg/cm$^2$ (ASTM D790), and Elongation at break; 500% (ASTMD638)] was used for the polymer (high-strength polymer) for the base layer (inner layer).

A polyester elastomer [TOYOBO Co., Ltd., Product Name: PELPRENE P-150B, Polyester elastomer with an aromatic polyester as the hard segment and an aliphatic polyether as the soft segment, Tensile fracturing strength: 390 kg/cm$^2$ (ASTM D638), Modulus of flexural elasticity: 2,950 kg/cm$^2$ (ASTM D790), and elongation at break: 550% (ASTM D638)] was used for the polymer (flexible polymer) for forming the covering layer (outer layer).

A two-layer tube with a PET layer (base layer) inside and a polyester layer (covering layer) outside was made by coextrusion used in a usual wire-covering process using the above polymers. The interior diameter of the tube was 0.45 min, and the exterior diameter was 0.85 mm. The thickness of the inner layer was 0.11 mm, and that of the outer layer was 0.09 mm. The ratio of the sectional area of the inner layer to that of the outer layer (this becomes the ratio of wall thickness of the balloon made from this tube) was 1/1.

This tube was put into a metal mold as shown in FIG. 4 and heated to 150° C. The tube was stretched to about twice the original length in the axial direction, and then inflated and tightly pressed against the inside surface of the metal mold by introducing air into it. Thus the basic shape of the balloon was formed. The expansion ratio in the radial direction was about 6 times for the interior radius and about 3 times for the exterior radius. This balloon was then inflated with a pressure of 1 kg/cm$^2$ in water at 37° C. by means of nitrogen gas. The exterior diameter of the balloon (cylindrical portion) was 2.85 mm, and the wall thickness of the portion with the largest exterior diameter (cylindrical portion) was 10 µm. The thickness of the PET layer of the portion with the largest exterior diameter (cylindrical portion) was 5 µm

EXAMPLE 2

A two-layer tube of the same dimensions as those of the tube of Example 1 was made by the same process as that of Example 1 except that a different polyester elastomer [TOYOBO Co., Ltd., Product Name: PELPRENE P-450B, Polyester elastomer with an aromatic polyester as the hard segment and an aliphatic polyether as the soft segment, Tensile fracturing strength: 354 kg/cm$^2$ (ASTM D638), Flexural elasticity: 12,930 kg/cm$^2$ (ASTM D790), and Elongation at break: 440% (ASTM D638)] was used for the polymer (flexible polymer) for forming the covering layer (outer layer).

A balloon was made of this tube by the same process as that of example 1. The exterior diameter of the balloon was 0.85 mm. The thickness of the inner layer was 0.11 mm, and that of the outer layer was 0.09 mm. This balloon was then inflated with a pressure of 1 kg/cm$^2$ in water at 37° C. by means of nitrogen gas. The exterior diameter of the balloon was 2.85 mm, and the wall thickness of the portion with the largest exterior diameter (cylindrical portion) was 10 µm.

EXAMPLE 3

A two-layer Lube with an interior diameter of 0.45 mm, exterior diameter of 0.91 mm, and ratio of the sectional area of the inner layer to that of the outer layer of 1/1.5 was made of the same materials as those of Example 1.

Next, a balloon was made by the same process as that of Example 1. This balloon was then inflated with a pressure of 1 kg/cm$^2$ in water at 37° C. by means of nitrogen gas. The thickness of the polyethylene terephthalate layer was 5 µm and that of polyester elastomer layer was 7.5 µm, and the exterior diameter of the balloon was 2.85 mm, at the portion of the balloon with the largest exterior diameter.

EXAMPLE 4

A two-layer tube with a PET layer (base layer) outside and a polyester elastomer layer (covering layer) inside was made by coextrusion of the same polymers as those of Example 1. The interior diameter of the tube was 0.45 mm, and the exterior diameter was 0.85 mm. The thickness of the inner layer was 0.11 mm, and that of the outer layer was 0.09 mm. The ratio of the sectional area of the inner layer to that of the outer layer was 1/1.

A balloon was made of this tube by the same process as that of Example 1. This balloon was then inflated with a pressure of 1 kg/cm$^2$ in water at 37° C. by means of nitrogen gas The exterior diameter of the balloon was 2.85 mm, and the wall thickness of the portion with the largest exterior diameter (cylindrical portion) was 10 µm.

EXAMPLE 5

A three-layer tube with a PET layer (base layer) as a middle layer and polyester elastomer layers (covering layers) as an outer and inner layers was made by three-color extrusion used in a usual wire-covering process using the same polymers as those of Example 1. The interior diameter of the tube was 0.45 mm, and the exterior diameter was 0.85 mm. The thicknesses of the inner layer, middle layer, and outer layer were 0.05 mm, 0.10 mm, and 0.05 mm, respectively. The ratio of the sectional area of the middle layer to that of the inner and outer layers combined was 1/1.

This tube was put into a metal mold as shown in FIG. 4 and heated to 150° C. The tube was stretched to about twice the original length in the axial direction, and then inflated and tightly pressed against the inside surface of the metal mold by introducing air in it. Thus a balloon was obtained. The expansion ratio in the radial direction was about 6 times for the interior radius and about 3 times for the exterior radius. This balloon was then inflated with a pressure of 1 kg/cm² in water at 37 ° C. by means of nitrogen gas. The exterior diameter was 2.85 mm, and the wall thickness was 10 μm, at the portion with the largest exterior diameter.

Comparison Example 1

A single-layer tube with an interior diameter of 0.45 mm, exterior diameter of 0.67 mm, and wall thickness of 0.11 mm was made of the same PET as the one used in Example 1 by a wire-covering process.

A balloon was made of this tube by the same process as that of Example 1. This balloon was inflated with a pressure of 1 kg/cm² in water at 37° C. by means of nitrogen gas. The exterior diameter was 2.85 mm, and the wall thickness was 5 μm, at the portion of the balloon with the largest exterior diameter.

Comparison Example 2

A two-layer tube of the same dimensions as those of the tube of Example 1 was made by the same process as that of Example 1 except that a straight-chain low-density polyethylene [Mitsubishi Chemical Corporation, Product Name: MITUBISHI POLYETHYC6, SF520, Elongation at break: 800% (ASTM D638)] was used for the polymer (flexible polymer) for forming the covering layer (outer layer).

A balloon was made of this tube by the same process as that of example 1 except that the heat-setting temperature was 105° C. This balloon was then inflated with a pressure of 1 kg/cm² in water at 37° C. by means of nitrogen gas. The exterior diameter of the balloon was 2.85 mm, and the wall thickness of the portion with the largest exterior diameter (cylindrical portion) was 10 μm.

Experiment 1

The bursting strength of the balloons obtained in Examples 1 to 5 and Comparison Examples 1 and 2 was measured in water at 37° C. by blowing nitrogen gas into them with a pressure increased by 1 kg/cm² increments. Table 1 below shows the results.

TABLE 1

|  | Bursting Strength | Percentage of Bursting Stress Born by Covering Layer |
|---|---|---|
| Example 1 | 18 kg/cm² | 28% |
| Example 2 | 19 kg/cm² | 32% |
| Example 3 | 20 kg/cm² | 35% |
| Example 4 | 18 kg/cm² | 28% |
| Example 5 | 18 kg/cm² | 28% |
| Comparison Example 1 | 13 kg/cm² | — |
| Comparison Example 2 | 14 kg/cm² | 7% |

Although the balloons of Example 1 and Comparison Example 2 have the base layer and covering layer of the same thickness (5 μm), the stress born by the covering layer (polyester elastomer layer) of the balloon of Example 1 was 5 kg/cm², whereas that born by the covering layer (straight-chain low-density polyethylene) of the balloon of Comparison Example 2 was 1 kg/cm². The percentages of the bursting stress born by the covering layer of these balloons were about 28% and about 7%, respectively. The same percentage was calculated on the other sample balloons.

The wall strength of each layer was then calculated using the following known film equation (refer to Japan Patent Application Publication Gazette (J.P.B.) 1990-28341 and Japan Patent Application Lay-open Gazette (J.P.A.) 1987-183070):

$$S = 1000 \times P \times D / 2t \qquad \text{(Film equation)},$$

where S is the wall strength (kg/cm²), P is the internal pressure when the balloon bursts (kg/cm²), D is the exterior diameter (mm) of the balloon when a pressure of 1 kg/cm² is applied, and t is the wall thickness of the portion of the balloon with the largest exterior diameter. S (wall strength) was calculated by the Film equation. S of polyester elastomer layer of the balloon of Example is 1425 kg/cm². S of the straight-chain low-density polyethylene layer of the balloon of Comparative Example 2 is 285 kg/cm².

The polyester elastomer showed an expected large strength. On the other hand, the stress the straight-chain low-density polyethylene bore when the balloon burst was far smaller than the fracturing strength (390 kg/cm²) in the specification, being an intermediate value between the yield-point strength (140 kg/cm²) and the fracturing strength The reason is thought to be as follows. The maximum extension (fracturing-point extension) of PET is smaller than that of the straight-chain low-density polyethylene, and hence the PET layer reaches its maximum extension earlier than the straight-chain low-density polyethylene layer and fractures when an increasing pressure is applied to the inside of the balloon. Once the PET layer fractures, all the pressure is applied to the straight-chain low-density polyethylenes layer, and the straight-chain low-density polyethylene layer cannot withstand it alone and immediately fractures. As the result the stress born by the straight-chain low-density polyethylene layer when the balloon bursts (when the PET layer fractures, to be exact) is such a value far smaller than the fracturing strength.

It is thought that since the maximum extension (elongation at break) of the polyester elastomer is near that of PET and the temperature when the balloon was formed is lower than the fusing point of the polyester elastomer, the polyester elastomer layer was fixed in the condition in which it was put by being biaxially stretched in the shape of a balloon, and therefore the strength of the polyester elastomer layer calculated from the measurements was much larger than the fracturing strength in the specification.

EXAMPLE 6

A polyamide [EMS-CHEMIE AG, Product Name: GRYLAMID L25, 12-nylon, Tensile fracturing strength: 500 kg/cm² (ASTM D638), Flexural elasticity: 12,000 kg/cm² (ASTM D790), and Elongation at break: 270% (ASTM D638)] was used for the polymer (high-strength polymer) for forming the base layer (inner layer).

A polyamide elastomer [Atochem Corp., Product Name: PEPAX 6333SA01, Polyamide elastomer with a polyamide as the hard segment and an aliphatic polyether as the soft segment, Tensile fracturing strength: 520 kg/cm² (ASTM D638), Flexural elasticity: 3,500 kg/cm² (ASTM D790), and Elongation at break: 300% (ASTM D638)] was used for the polymer (flexible polymer) for forming the covering layer (outer layer).

A two-layer tube with a PET layer (base layer) inside and a polyester elastomer layer (covering layer) outside was made by coextrusion. The interior diameter of the tube was 0.45 mm, and the exterior diameter was 0.90 mm. The thickness of the inner layer was 0.18 mm, and that of the outer layer was 0.045 mm. The ratio of the sectional area of the inner layer to that of the outer layer was 3/1.

This tube was put into a metal mold as shown in FIG. 4 and heated to 140° C. The tube was stretched to about 1.8 times the original length in the axial direction, and then inflated and tightly pressed against the inside surface of the metal mold by introducing air into it. Thus the basic shape of the balloon was formed. The expansion ratio in the radial direction was about 5.5 times for the interior radius and about 2.8 times for the exterior radius. This balloon was then inflated with a pressure of 1 kg/cm$^2$ in water at 37° C. by means of nitrogen gas. The exterior diameter of the balloon was 2.52 mm, and the wall thickness of the portion with the largest exterior diameter (cylindrical portion) was 20 μm.

EXAMPLE 7

A two-layer tube with an interior diameter of 0.45 mm, exterior diameter of 0.98 mm, inner-layer thickness of 0.24 mm, outer-layer thickness of 0.085 mm, and inner-layer and outer-layer sectional area ratio of 3/2 was made of the same materials as those of Example 6.

Next, a balloon was made by the same process as that of Example 1. This balloon was then inflated with a pressure of 1 kg/cm$^2$ in water at 37° C. by means of nitrogen gas. The thicknesses of the polyamide layer and the polyamide elastomer layer was 15 μm and 10 μm, respectively, and the exterior diameter of the balloon was 2.52 mm, at the portion of the balloon with the largest exterior diameter.

EXAMPLE 8

A two-layer tube with a polyamide layer (base layer) outside and a polyamide elastomer layer (covering layer) inside was made by coextrusion of the same polymers as those of Example 6. The interior diameter of the tube was 0.45 mm, and the exterior diameter was 0.90 mm. The thickness of the inner layer was 0.075 mm, and that of the outer layer was 0.15 mm. The ratio of the sectional area of the inner layer to that of the outer layer was 1/3.

A balloon was made of this tube by the same process as that of Example 6. This balloon was then inflated with a pressure of 1 kg/cm$^2$ in water at 37° C. by means of nitrogen gas. The exterior diameter was 2.52 mm, and the wall thickness was 10 μm, at the portion of the balloon with the largest exterior diameter.

EXAMPLE 9

A three-layer tube with a polyamide layer (base layer) as the middle layer and a polyamide elastomer layer (covering layer) as the outer and inner layers was made by three-color extrusion used in a usual wire-covering process using the same polymers as those of Example 6. The interior diameter of the tube was 0.45 mm, and the exterior diameter was 0.90 mm. The thicknesses of the inner layer, middle layer, and outer layer were 0.025 mm, 0.17 mm, and 0.03 mm, respectively. The ratio of the sectional area of the middle layer to that of the inner and outer layers combined was 3/1.

A balloon was made of this tube by the same process as that of Example 1. This balloon was inflated with a pressure of 1 kg/cm$^2$ in water at 37° C. by means of nitrogen gas. The exterior diameter was 2.52 mm, and the wall thickness was 20 μm, at the portion of the balloon with the largest exterior diameter.

Comparison Example 3

A single-layer tube with an interior diameter of 0.45 mm, exterior diameter of 0.81 mm, and wall thickness of 0.18 mm was made by a wire-covering process using the same polyamide as the one used in Example 1.

A balloon was made of this tube by the same process as that of Example 1. This balloon was inflated with a pressure of 1 kg/cm$^2$ in water at 37° C. by means of nitrogen gas. The exterior diameter was 2.52 mm, and the wall thickness was 15 μm, at the portion of the balloon with the largest exterior diameter.

Experiment 2

The bursting strength of the balloons obtained in Examples 6 to 9 and Comparison Example 3 was measured in water at 37° C. by blowing nitrogen gas into them with a pressure increased by 1 kg/cm$^2$ increments. In addition, what percentage of the bursting stress was born by the covering layer of these balloons was calculated from the measurements. Table 2 below shows the results.

TABLE 2

|  | Bursting Strength | Percentage of Bursting Stress Born by Covering Layer |
|---|---|---|
| Example 6 | 22 kg/cm$^2$ | 13.6% |
| Example 7 | 25 kg/cm$^2$ | 24.0% |
| Example 8 | 22 kg/cm$^2$ | 13.6% |
| Example 9 | 22 kg/cm$^2$ | 13.6% |
| Comparison Example 3 | 19 kg/cm$^2$ | — |

EXAMPLE 10

A high-molecular polyethylene terephthalate (PET) with a specific viscosity of about 1.1[JAPAN UNIPET Co., Ltd., Product Name: UNIPET RT580CA, Tensile fracturing strength: 600 kg/cm$^2$ (ASTM D638), Modulus of flexural elasticity: 24,000 kg/cm$^2$ (ASTM D790), and Elongation at break: 500% (ASTM D638)] was used for the polymer (high-strength polymer) for forming the base layer (inner layer).

A polyester elastomer [TOYOBO Co., Ltd., Product Name: PELPRENE P-150B, Polyester elastomer with an aromatic polyester as the hard segment and an aliphatic polyether as the soft segment, Tensile fracturing strength: 390 kg/cm$^2$ (ASTM D638), Modulus of flexural elasticity: 2,950 kg/cm$^2$ (ASTM D790), and Elongation at break: 550% (ASTM D638)] was used for the polymer (flexible polymer) for forming a first covering layer (middle layer).

A polyester elastomer [TOYOBO Co., Ltd., Product Name: PELPRENE P-150M, Polyester elastomer with an aromatic polyester as the hard segment and an aliphatic polyether as the soft segment, Tensile fracturing strength: 380 kg/cm$^2$ (ASTM D638), Modulus of flexural elasticity: 1,200 kg/cm$^2$ (ASTM D790), and Elongation at break: 420% (ASTM D638)] was used for the polymer (high-flexibility polymer) for forming a second covering layer (outer layer).

A three-layer tube with a PET layer (base layer) inside, a layer of the first polyester elastomer layer (first covering layer) at the middle, and a layer of the second polyester elastomer (second covering layer) outside was made by three-color extrusion using the above polymers. The interior diameter of the tube was 0.30 mm, and the exterior diameter was 0.66 mm. The thicknesses of the inside layer (ease layer), middle layer (first covering layer), and outside layer (second covering layer) were 0.1 mm, 0.03 mm, and 0.05 mm, respectively.

This tube was put into a metal mold as shown in FIG. 4 and heated to 150° C. The tube was stretched to twice the original length in the axial direction, and then inflated and tightly pressed against the inside surface of the metal mold by introducing air into it. Thus the balloon was formed. The expansion ratio in the radial direction was about 6 times for the interior radius and about 3 times for the exterior radius. This balloon was then inflated with a pressure of 1 kg/cm$^2$ in water at 37° C. by means of nitrogen gas. The exterior diameter was 2.0 mm, and the wall thickness was 12 $\mu$m, at the portion of the balloon with the largest exterior diameter. The thicknesses of the inside layer (base layer), middle layer (first covering layer), and outside layer (second covering layer) were 5 $\mu$m, 2 $\mu$m, and 5 $\mu$m, respectively. at the same portion of the balloon.

EXAMPLE 11

A three-layer tube with a PET layer (base layer) inside, a layer of the first polyester elastomer (first covering layer) at the middle, and a layer of the second polyester elastomer (second covering layer) outside was made by three-color extrusion using the same polymers as those of Example 10. The interior diameter of the tube was 0.42 mm, and the exterior diameter was 0.8 mm. The thicknesses of the inside layer (base layer), middle layer (first covering layer), and outside layer (second covering layer) were 0.095 mm, 0.025 mm, and 0.07 mm, respectively.

A balloon was made of this tube by the same process as that of example 10. The expansion ratio in the radial direction was about 6 times for the interior radius and about 3 times for the exterior radius. This balloon was then inflated with a pressure of 1 kg/cm$^2$ in water at 37° C. by means of nitrogen gas. The exterior diameter was 2.5 mm, and the wall thickness was 13.5 $\mu$m, at the portion with the largest exterior diameter. The thicknesses of the inside layer (base layer), middle layer (first covering layer), and outside layer (second covering layer) were 6 $\mu$m, 2 $\mu$m, and 5.5 $\mu$m, respectively.

EXAMPLE 12

A three-layer tube with a PET layer (base layer) inside, a layer of the first polyester elastomer (first covering layer) at the middle, and a layer of the second polyester elastomer (second covering layer) outside was made by three-color extrusion using the same polymers as those of Example 10. The interior diameter of the tube was 0.45 mm, and the exterior diameter was 0.9 mm. The thicknesses of the inside layer (base layer), middle layer (first covering layer), and outside layer (second covering layer) were 0.11 mm, 0.035 mm, and 0.08 mm, respectively.

A balloon was made of this tube by the same process as that of example 10. The expansion ratio in the radial direction was about 6 times for the interior radius and about 3 times for the exterior radius. This balloon was inflated with a pressure of 1 kg/cm$^2$ in water at 37° C. by means of nitrogen gas. The exterior diameter was 2.75 mm, and the wall thickness was 16.0 $\mu$m, at the portion with the largest exterior diameter. The thicknesses of the inside layer (base layer), middle layer (first covering layer), and outside layer (second covering layer) were 6.5 $\mu$m, 2.5 $\mu$m, and 7 $\mu$m, respectively.

EXAMPLE 13

A three-layer tube with a PET layer (base layer) inside, a layer of the first polyester elastomer (first covering layer) at the middle, and a layer of the second polyester elastomer (second covering layer) outside was made by three-color extrusion using the same polymers as those of Example 10. The interior diameter of the tube was 0.5 mm, and the exterior diameter was 1.0 min. The thicknesses of the inside layer (base layer), middle layer (first covering layer), and outside layer (second covering layer) were 0.115 mm, 0.035 mm, and 0.1 mm, respectively.

A balloon was made of this tube by the same process as that of example 10. The expansion ratio in the radial direction was about 6 times for the interior radius and about 3 times for the exterior radius. This balloon was inflated with a pressure of 1 kg/cm$^2$ in water at 37° C. by means of nitrogen gas. The exterior diameter was 3.0 mm, and the wall thickness was 17.0 $\mu$m, at the portion with the largest exterior diameter. The thicknesses of the inside layer (base layer), middle layer (first covering layer), and outside layer (second covering layer) were 6.5 $\mu$m, 2.5 $\mu$m, and 8 $\mu$m, respectively.

EXAMPLE 14

A three-layer tube with a PET layer (base layer) inside, a layer of the first polyester elastomer (first covering layer) at the middle, and a layer of the second polyester elastomer (second covering layer) outside was made by three-color extrusion using the same polymers as those of Example 10. The interior diameter of the tube was 0.53 mm, and the exterior diameter was 1.05 mm. The thicknesses of the inside layer (base layer), middle layer (first covering layer), and outside layer (second covering layer) were 0.12 mm, 0.04 mm, and 0.1 mm, respectively.

A balloon was made of this tube by the same process as that of example 10. The expansion ratio in the radial direction was about 6 times for the interior radius and about 3 times for the exterior radius. This balloon was inflated with a pressure of 1 kg/cm$^2$ in water at 37° C. by means of nitrogen gas. The exterior diameter was 3.25 mm, and the wall thickness was 19.0 $\mu$m, at the portion with the largest exterior diameter. The thicknesses of the inside layer (base layer), middle layer (first covering layer), and outside layer (second covering layer) were 7.0 $\mu$m, 3.0 $\mu$m, and 9 $\mu$m, respectively.

EXAMPLE 15

A three-layer tube with a PET layer (base layer) inside, a layer of the first polyester elastomer (first, covering layer) at the middle, and a layer of the second polyester elastomer (second covering layer) outside was made by three-color extrusion using the same polymers as those of Example 10. The interior diameter of the tube was 0.55 mm, and the exterior diameter was 1.10 mm. The thicknesses of the inside layer (base layer), middle layer (first covering layer), and outside layer (second covering layer) were 0.125 mm, 0.05 mm, and 0.1 mm, respectively.

A balloon was made of this tube by the same process as that of example 10. The expansion ratio in the radial direction was about 8 times for the interior radius and about 3.5 times for the exterior radius. This balloon was inflated with a pressure of 1 kg/cm$^2$ in water at 37° C. by means of nitrogen gas. The exterior diameter was 3.5 mm, and the wall thickness was 20.0 $\mu$m, at the portion with the largest exterior diameter. The thicknesses of the inside layer (base layer), middle layer (first covering layer), and outside layer (second covering layer) were 7.5 $\mu$m, 3.5 $\mu$m, and 9 $\mu$m, respectively.

Experiment 3

The bursting strength of the balloons obtained in Examples 10 to 15 was measured in water at 37 ° C. by blowing nitrogen gas into them with a pressure increased by 1 kg/cm² increments. Table 3 below shows the results.

TABLE 1

|  | Bursting Strength | Percentage of Bursting Stress Born by Covering Layer |
|---|---|---|
| Example 10 | 24 kg/cm² | 23% |
| Example 11 | 23 kg/cm² | 23% |
| Example 12 | 22 kg/cm² | 20% |
| Example 13 | 21 kg/cm² | 24% |
| Example 14 | 20 kg/cm² | 20% |
| Example 15 | 20 kg/cm² | 20% |

Note: The percentage of the bursting stress born by the covering layer was the combined percentage born by the first and second covering layers.

As understood from the above detailed description, by selecting an appropriate combination of the high-strength polymer for the base layer and the flexible polymer or polymers for one or more cover layers so that the covering layer or covering layers together bear significant part of the bursting stress, the object of this invention of providing an improved catheter balloon which has a high strength and a satisfactory high flexibility together can be attained. Moreover, the wall thickness of the balloon of this invention is made thicker compared with that of a single-layer balloon made of a high-strength polymer, the resistance to pinholes is greatly increased.

The balloon catheter of this invention is equipped with an improved catheter balloon of this invention. Since the balloon has a high flexibility, insertion of the catheter into a tubular organ such as a blood vessel is made easier. Further, since the catheter balloon a high strength, dilatation of a stenosed part can be performed with a sufficiently high inflating pressure, and therefore dilatation cab be made without failure.

Having illustrated and described the principles of our inventions in preferred embodiments thereof, it should be readily apparent to those skilled in the art that the inventions can be modified in arrangement and detail without departing from such principles. We do claim all those modifications coming within the sprit and scope of the accompanying claims.

What is claimed is:

1. A catheter balloon comprising a cylindrical portion and attaching portions for a catheter, said catheter balloon having a base layer formed of a high-strength polymer and one or more covering layers formed over at least one surface of said base layer of the same flexible polymer or different flexible polymers having a ratio of the elongation at break of the high-strength polymer to that of the flexible polymer within a range from about 1:0.7 to 1:1.3 and being more flexible than said high-strength polymer, and said cylindrical portion having a wall thickness of 25 μm or thinner.

2. The catheter balloon of claim 1 wherein said covering layer is formed over both surfaces of said base layer.

3. The catheter balloon of claim 1 which is biaxially stretched in the axial direction and circumferential direction.

4. The catheter balloon of claim 1 wherein said one or more flexible polymers are of the same polymer group as said high-strength polymer.

5. The catheter balloon of claim 4 wherein said high-strength polymer is polyethylene terephthalate and said flexible polymer is a polyester elastomer.

6. The catheter balloon of claim 4 wherein said high-strength polymer is a polyamide and said flexible polymer is a polyamide elastomer.

7. The catheter balloon of claim 1 wherein the difference of tensile fracturing strength between said high-strength polymer and said flexible polymer is 30% or smaller.

8. The catheter balloon of claim 1 wherein said base layer is inside and said covering layer is outside.

9. A catheter balloon comprising a cylindrical portion and attaching portions for a catheter, said catheter balloon having a base layer formed of a high-strength polymer and one or more covering layers formed over at least one surface of said base layer of the same flexible polymer or different flexible polymers more flexible than said high-strength polymer, and said covering layer or covering layers together bearing 10% or more part of the bursting stress of the balloon, and said cylindrical portion having a wall thickness of 25 μm or thinner.

10. The catheter balloon of claim 9 wherein said covering layer or covering layers together bear 20% or more part of the bursting stress of the balloon.

11. The catheter balloon of claim 9 wherein said covering layer is formed over both surfaces of said base layer.

12. The catheter balloon of claim 9 which is biaxially stretched in the axial direction and circumferential direction.

13. The catheter balloon of claim 9 wherein said one or more flexible polymers are of the same polymer group as said high-strength polymer.

14. The catheter balloon of claim 9 wherein said high-strength polymer is polyethylene terephthalate and said flexible polymer is a polyester elastomer.

15. The catheter balloon of claim 9 wherein said high-strength polymer is a polyamide and said flexible polymer is a polyamide elastomer.

16. The catheter balloon of claim 9 wherein the difference of a tensile fracturing strength between said high-strength polymer and said flexible polymer is 30% or smaller.

17. The catheter balloon of claim 9 wherein the difference of a elongation at break between said high-strength polymer and said flexible polymer is 30% or smaller.

18. The catheter balloon of claim 9 wherein said base layer is inside and said covering layer is outside.

19. A catheter balloon comprising a cylindrical portion and attaching portions for a catheter, said catheter balloon having a base layer formed of a high-strength polymer, a first covering layer formed over the outside surface of said base layer of an flexible polymer having a ratio of the elongation at break of the high-strength polymer to that of the flexible polymer within a range from about 1:0.7 to 1:1.3 and being more flexible than the high-strength polymer, and a second covering layer formed over the outside surface of said first covering layer of another flexible polymer more flexible than said flexible polymer for said first covering layer.

20. The catheter balloon of claim 19 wherein said cylindrical portion has a wall thickness of 25 μm or thinner.

21. The catheter balloon of claim 19 wherein said first covering layer bears 10% or more part of the bursting stress of the balloon.

22. The catheter balloon of claim 19 wherein said first covering layer bears 20% or more part of the bursting stress of the balloon.

23. The catheter balloon of claim 19 which is biaxially stretched in the axial direction and circumferential direction.

24. The catheter balloon of claim 19 wherein said one or more flexible polymers are of the same polymer group as said high-strength polymer.

25. The catheter balloon of claim 19 wherein said high-strength polymer is polyethylene terephthalate and said flexible polymer is a polyester elastomer.

26. The catheter balloon of claim 19 wherein said high-strength polymer is a polyamide and said flexible polymer is a polyamide elastomer.

27. The catheter balloon of claim 19 wherein the difference of a tensile fracturing strength between said high-strength polymer and said flexible polymer is 30% or smaller.

28. A balloon catheter comprises of a tubular catheter body and a balloon attached to a distal end portion of said tubular catheter body, and said balloon comprising a cylindrical portion and attaching portions for a catheter, said catheter balloon having a base layer formed of a high-strength polymer and one or more covering layers formed over at least one surface of said base layer of the same flexible polymer or different flexible polymers having a ratio of the elongation at break of the high-strength polymer to that of the flexible polymer within a range from about 1:0.7 to 1:1.3 and being more flexible than said high-strength polymer, and said cylindrical portion having a wall thickness of 25 μm or thinner.

29. The balloon catheter of claim 28 wherein the difference of tensile fracturing strength between said high-strength polymer and said flexible polymer is 30% or smaller.

30. The balloon catheter of claim 28 wherein said tubular catheter body comprising an inner tube with a first lumen open at a distal end and an outer tube which forms a second lumen between its inside surface and an outside surface of said inner tube and have a distal end retreated from the distal end of said inner tube by a predetermined distance, and said balloon whose front and rear end portions are attached to a distal end portions of said inner and outer tubes, respectively, and whose an inside space connects with said second lumen.

31. A balloon catheter comprises of a tubular catheter body and a balloon attached to a distal end portion of said tubular catheter body, and said balloon comprising a cylindrical portion and attaching portions for a catheter, said catheter balloon having a base layer formed of a high-strength polymer and one or more covering layers formed over at least one surface of said base layer of the same flexible polymer or different flexible polymers more flexible than said high-strength polymer, and said covering layer or covering layers together bearing 10% or more part of the bursting stress of the balloon, and said cylindrical portion having a wall thickness of 25 μm or thinner.

32. The balloon catheter of claim 31 wherein said covering layer or covering layers together bear 20% or more part of the bursting stress of the balloon.

33. The balloon catheter of claim 31 wherein said tubular catheter body comprising an inner tube with a first lumen open at a distal end and an outer tube which forms a second lumen between its inside surface and an outside surface of said inner tube and have a distal end retreated from the distal end of said inner tube by a predetermined distance, and said balloon whose front and rear end portions are attached to a distal end portions of said inner and outer tubes, respectively, and whose an inside space connects with said second lumen.

34. A balloon catheter comprises of a tubular catheter body and a balloon attached to a distal end portion of said tubular catheter body, and said balloon comprising a cylindrical portion and attaching portions for a catheter, said catheter balloon having a base layer formed of a high-strength polymer, a first covering layer formed over the outside surface of said base layer of an flexible polymer having a ratio of the elongation at break of the high-strength polymer to that of the flexible polymer within a range from about 1:0.7 to 1:1.3 and being more flexible than the high-strength polymer, and a second covering layer formed over the outside surface of said first covering layer of another flexible polymer more flexible than said flexible polymer for said first covering layer.

35. The balloon catheter of claim 34 wherein said cylindrical portion has a wall thickness of 25 μm or thinner.

36. The balloon catheter of claim 34 wherein the difference of tensile fracturing strength between said high-strength polymer and said flexible polymer is 30% or smaller.

37. The balloon catheter of claim 34 wherein said tubular catheter body comprising an inner tube with a first lumen open at a distal end and an outer tube which forms a second lumen between its inside surface and an outside surface of said inner tube and have a distal end retreated from the distal end of said inner tube by a predetermined distance, and said balloon whose front and rear end portions are attached to a distal end portions of said inner and outer tubes, respectively, and whose an inside space connects with said second lumen.

\* \* \* \* \*

UNITED STATES PATENT AND TRADEMARK OFFICE
CERTIFICATE OF CORRECTION

PATENT NO. : 5,879,369
DATED : March 9, 1999
INVENTOR(S) : T. ISHIDA

It is certified that error appears in the above-identified patent and that said Letters Patent is hereby corrected as shown below:

In column 4, line 59, delete "polymer or" and insert --polymer. For--
In column 5, line 41, delete "it" and insert --at--.
In column 11, line 57, delete "min," and insert --mm,--
In column 12, line 34, delete "Lube" and insert --tube--.
In column 16, line 64, delete "(ease" and insert --(base--.

Signed and Sealed this

Twenty-first Day of September, 1999

Attest:

Q. TODD DICKINSON

*Attesting Officer*     *Acting Commissioner of Patents and Trademarks*